United States Patent [19]
Zinnanti

[11] Patent Number: 5,449,357
[45] Date of Patent: * Sep. 12, 1995

[54] ENDOSCOPIC SUCTION, IRRIGATION AND CAUTERY INSTRUMENT

[76] Inventor: William J. Zinnanti, 3815 Northland, Newbury Park, Calif. 91320

[*] Notice: The portion of the term of this patent subsequent to Sep. 20, 2011 has been disclaimed.

[21] Appl. No.: 202,801

[22] Filed: Feb. 28, 1994

Related U.S. Application Data

[63] Continuation-in-part of Ser. No. 51,546, Apr. 26, 1993, Pat. No. 5,348,555.

[51] Int. Cl.6 ............................................. A61B 17/39
[52] U.S. Cl. ....................................... 606/49; 604/21; 604/33; 606/45
[58] Field of Search ........................ 604/33–35, 604/249, 275, 21, 27, 39, 43; 606/27–32, 37–42, 45–50

[56] References Cited

U.S. PATENT DOCUMENTS

| | | | |
|---|---|---|---|
| 2,669,233 | 2/1954 | Friend | 604/33 |
| 3,478,743 | 11/1969 | Ericson | 604/33 |
| 3,835,842 | 9/1974 | Iglesias | 128/7 |
| 4,451,257 | 5/1984 | Atchley | 604/33 X |
| 5,163,926 | 11/1992 | Bailey | 604/35 X |
| 5,186,714 | 2/1993 | Boudreault et al. | 604/33 X |
| 5,188,591 | 2/1993 | Dorsey, III | 604/33 |
| 5,190,541 | 3/1993 | Abele et al. | 604/35 X |
| 5,195,958 | 3/1993 | Phillips | 604/33 |

*Primary Examiner*—Stephen C. Pellegrino
*Assistant Examiner*—Michael Peffley
*Attorney, Agent, or Firm*—Allen A. Dicke, Jr.

[57] ABSTRACT

The cautery instrument body has finger-operated valves for respective connection to sources of suction and irrigation. The valve plungers each have at least one O-ring which engages against a shoulder on the body when the valves are closed to cause positive shutoff when the valves are unactuated. The suction control valve has an adjustable stop to limit valve opening to control suction. The body has connection ports on each end so that it is reversible and has a clear polymer cannula attached in one of the ports for endoscopic utilization. The other port carries a cautery rod which can be extended out of the cannula. The suction and irrigation valves, the adjustable suction stop, and the cautery rod are all positioned so that they can be operated by the fingers of the hand which holds the body of the instrument.

15 Claims, 4 Drawing Sheets

ENDOSCOPIC SUCTION, IRRIGATION AND CAUTERY INSTRUMENT

CROSS-REFERENCE

This application is a continuation-in-part of my earlier application, Ser. No. 08/051,546, filed Apr. 26, 1993 for "Endoscopic Suction, Irrigation and Cautery Instrument," now U.S. Pat. No. 5,348,555.

FIELD OF THE INVENTION

This invention is in the field of endoscopic medical instruments which are used through an abdominal (or other) port to perform suction, irrigation and cautery functions within the body.

BACKGROUND OF THE INVENTION

Modern advances in surgical techniques have resulted in laparoscopic surgery. The patient is grounded; a plastic trochar port is placed in the abdominal wall; and the abdomen is distended by insufflation of carbon dioxide. This is done to open up the space between the organs where the endoscope and the laparoscopic instruments are manipulated. The common cannula through which the cautery electrode is passed is made of metal. Even though the electrode is electrically insulated, an electrical charge is capacitively coupled to the metal cannula. The metal cannula is not grounded, but the patient's body is grounded for monopolar cautery technique. When a cautery charge is applied through the cautery electrode, a capacitively coupled charge is created in the metal cannula. When the metal cannula is touching tissue inside the abdominal cavity, the capacity coupled charge can cause the metal cannula to burn tissue with which it is in contact. Since this burn is in an area unexpected by the surgeon, often it goes undetected. This is one of the major causes of post-surgery morbidity and infection resulting from laparoscopic surgery. During the procedure, the surgeon must place the cautery electrode at the site. In order to permit unobstructed viewing, irrigation and suction are often necessary to wash the area and to withdraw liquid, vapor and smoke which result from the cautery procedure. Proper control of the irrigation and suction is necessary for proper viewing in the area where the procedure is taking place. The suction and irrigation valves must be easily operable and must be fully closed when unactuated. Furthermore, the actuation controls of the valves, the suction valve stop, and the cautery instrument should be close together so that they can be operated by the fingers of the hand which holds and manipulates the instrument. Thus, there is need for improvement in endoscopic cautery instruments.

SUMMARY OF THE INVENTION

In order to aid in the understanding of this invention, it can be stated in essentially summary form that it is directed to an endoscopic suction, irrigation and cautery instrument wherein the valve body carries suction and irrigation control valves which have O-rings thereabout for positive closing for complete shutoff. The body is the same on both ends so that the cannula can be attached at either end. The opposite end carries a cautery electrode in the form of a rod which extends to the open tip end of the cannula. The cautery electrode can be manipulated to be exposed or retracted.

It is, thus, an object and advantage of this invention to provide an endoscopic suction, irrigation and cautery instrument which can be manipulated to perform its suction, irrigation or cautery functions in laparoscopic surgery, including utilization of a dielectric lumen to avoid capacitive charge coupling to the lumen.

It is another object and advantage of this invention to provide an endoscopic suction instrument which has a transparent lumen and transparent valve body so that the progress of suction material can be observed.

It is a further object and advantage of this invention to provide an endoscopic suction and irrigation instrument which has separate plunger valves to control the irrigation and suction at the lumen end and which has O-rings and corresponding shoulders in the valves so that the valves have positive shutoff.

It is a further object and advantage of this invention to provide an endoscopic suction instrument for laparoscopic surgery which has an adjustable stop on the valve body held by the surgeon that the surgeon can control the amount of vacuum flow during use.

It is another object and advantage of this invention to provide valve plungers in the valve body, suction and irrigation connections to the valve body and a main passage all the way through the valve body with the main passage out of line with the suction and irrigation connection and the valve stems having diagonal openings therethrough to connect the connections to the main passage to enhance control of flow to and from the main passage.

It is another object and advantage of this invention to provide an endoscopic suction, irrigation and cautery instrument which is arranged so that it can be assembled for either right-hand or left-hand use.

It is a further object and advantage of this invention to provide an endoscopic suction instrument which is provided with interchangeable clear polymer lumens of different sizes so that large material such as blood clots and gallstones can be suctioned away, and a small lumen which may be employed for other use.

It is another object and advantage of this invention to provide an endoscopic suction, irrigation and cautery instrument wherein the cautery electrode extends through the clear polymer suction and irrigation lumen so that the lumen protects the cautery electrode, with the advance of the cautery electrode being controlled by the surgeon as he holds the body of the instrument.

Other objects and advantages of this invention will become apparent from a study of the following portion of the specification, the claims and the attached drawings.

DESCRIPTION OF THE PREFERRED EMBODIMENT

Figures 1, 2, 3:
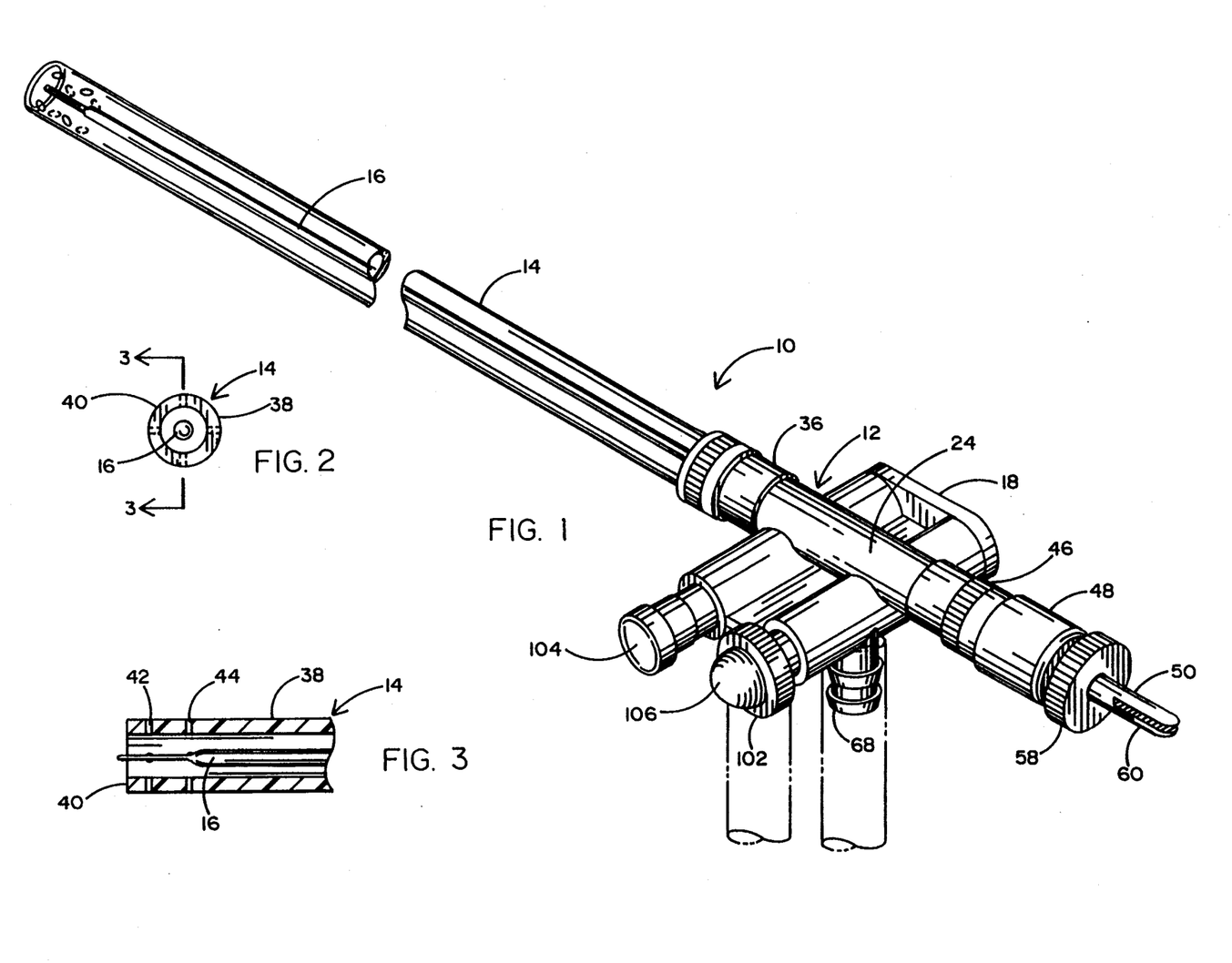
FIG. 1 is an isometric view of the endoscopic suction, irrigation and cautery instrument of this invention.
FIG. 2 is an enlarged end-elevational view of the lumen with the cautery electrode therein.
FIG. 3 is a section taken generally along line 3—3 of FIG. 2, with parts broken away.
Figure 4:
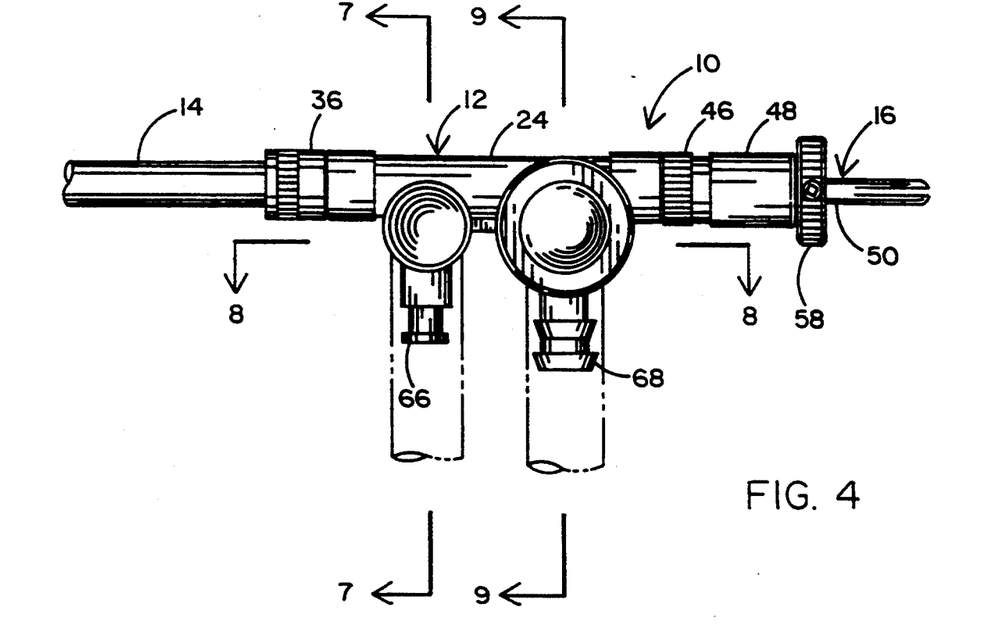
FIG. 4 is a side-elevational view of the instrument, with part of the lumen broken away.
Figure 5:
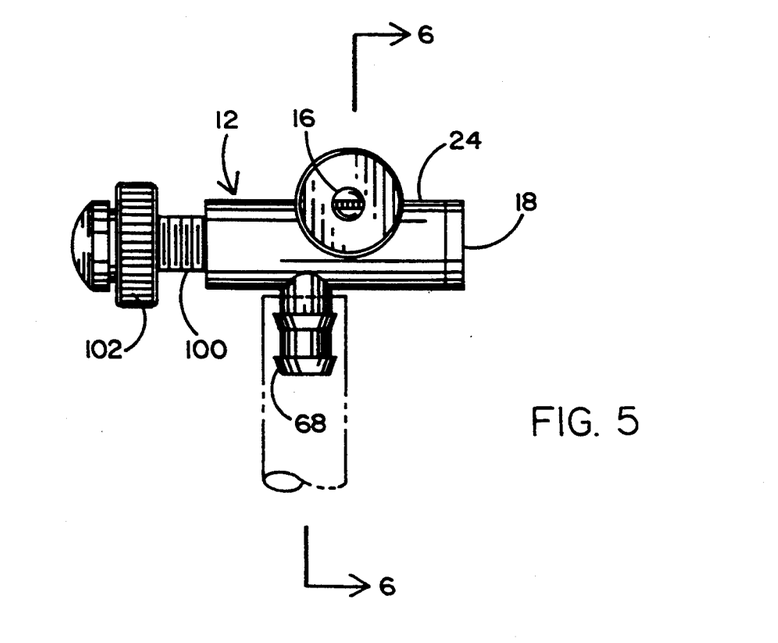
FIG. 5 is a rear-elevational view of the instrument, as seen from the right of FIG. 4.
Figure 6:
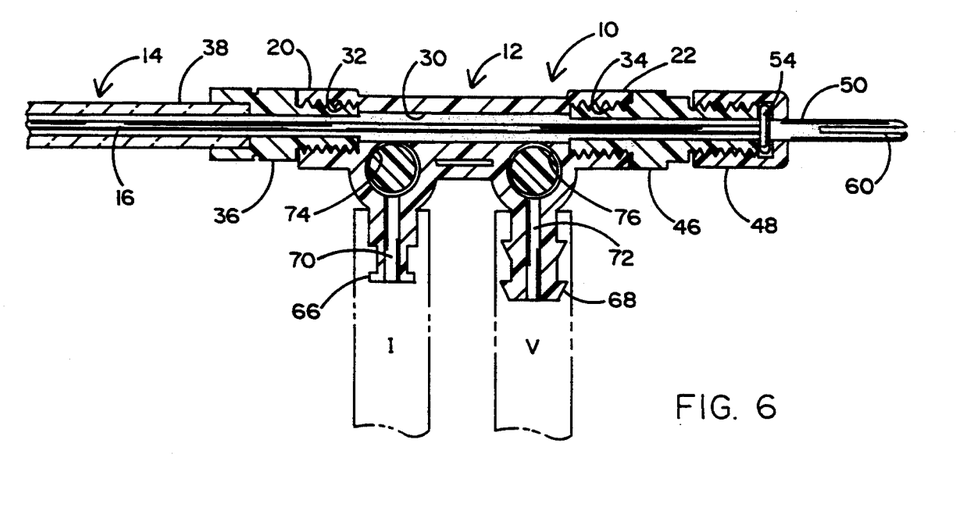
FIG. 6 is a section taken generally along line 6—6 of FIG. 5.

The endoscopic suction, irrigation and cautery instrument of this invention is generally indicated at 10 in FIG. 1. It is also shown in FIGS. 4 and 6 with part of the cannula broken away. The instrument 10 comprises a body 12, cannula 14 and cautery electrode 16. The body 12 is seen in section in FIGS. 6, 7 and 9. The body is made of transparent synthetic polymer composition material. The material must be fairly hard and rigid and must be capable of withstanding autoclave sterilization temperatures. Polycarbonate is suitable. The body has ends 20 and 22. The body is sized so that it may be engaged in the hand with the bottom 18 against the heel of the hand and the palm side 24 against the surgeon's palm with the surgeon's fingers extending around the valve side.

The body has a main passage through 30 therethrough (see FIGS. 6 and 9) which extends from end to end. At its ends, the main passage 30 has female threaded connection sockets 32 and 34 therein (see FIG. 6). These threaded sockets are identical, but on opposite ends of the body. Tubular fitting 36 has male threads thereon which engage into the socket 32. The tubular fitting is a fitting which carries cannula tube 38 thereon. The cannula is a clear polymer tube which extends to a face 40 (see FIGS. 2 and 3). Just behind the face are vent holes 42 and 44 which vent to permit the cannula to pull away even if the face is sucked against tissue. The cross holes extend all the way across the cannula tube and are also represented by further cross holes at right angles to the axial length of the tubular cannula 38. The cannula 38 can be a throwaway device and, thus, need not be subject to heat sterilization. The cannula 38 may be made of polyvinyl chloride, or similar material, or acrylic type materials. Since the sockets 32 and 34 are the same, the cannula may be installed in either end of the body.

In FIG. 1, it can be visualized that the body 12 is grasped in the surgeon's right hand with the heel of his hand against bottom 18, the palm of his hand against side 24, and his fingers available to actuate the valves on the near side. In such a circumstance, the cannula 38 extends substantially parallel to the surgeon's knuckle ridge in a direction away from his thumb. Should the surgeon desire to use the instrument in his left hand, the cannula can be placed in socket 34 so that the surgeon can grasp the body in his left hand in the same manner as previously described. In that case, the cannula 38 would extend generally parallel to the surgeon's knuckle ridge in the direction away from his thumb.

Cautery fitting 46 screws into the female threaded socket 34, as seen in FIG. 6. Fitting 46 has a male thread on the outer end thereof with cap 48 threaded thereon. The cap has an opening through which the shank 50 of cautery electrode 16 passes. An O-ring 54 engages around the shank 50 and is compressed at the end of fitting 46 to seal the opening and provide frictional resistance of movement of the cautery electrode with respect to the body 12 (see FIG. 6). Adjustment wheel 58 is fixed to the shaft 50. In the right-hand, recessed position of the cautery electrode 52, there is space between the wheel 58 and the cap 48. The adjustment wheel 58 is positioned so that it can be engaged by the thumb to rotate and advance the cautery electrode. The advancement limit is achieved by the adjustment wheel engaging on cap 48. Electrode connector 60 extends to the right of adjustment wheel 58 and is for electrical connection from a conventional cautery machine. Thus, by one-handed operation, the cannula 38 can be positioned and the cautery electrode extended or retracted with respect to the cannula.

Figure 7:
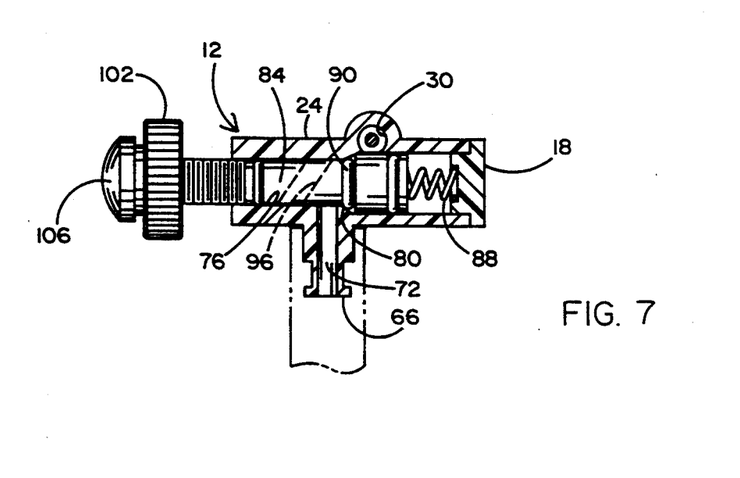
FIG. 7 is a section taken generally along line 7—7 of FIG. 4.
Figure 9:
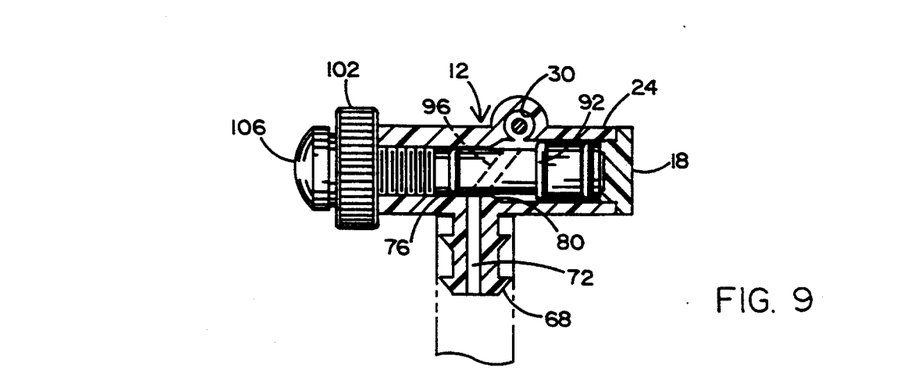
FIG. 9 is a section taken generally along line 9—9 of FIG. 4

The nipple side of the body has molded thereon two nipples 66 and 68, see FIGS. 6, 7 and 9. The nipples are barbed on the exterior to receive a flexible polymer hose. The nipples have openings therethrough for fluid connection with respect to the hose. Hoses are shown in dashed lines in FIGS. 1, 4, 5, 6, 7 and 9. The hose connected to nipple 66 is connected to supply irrigation fluid, such as saline solution. The hose connected to nipple 68 is connected to a source of vacuum.

Figure 8:
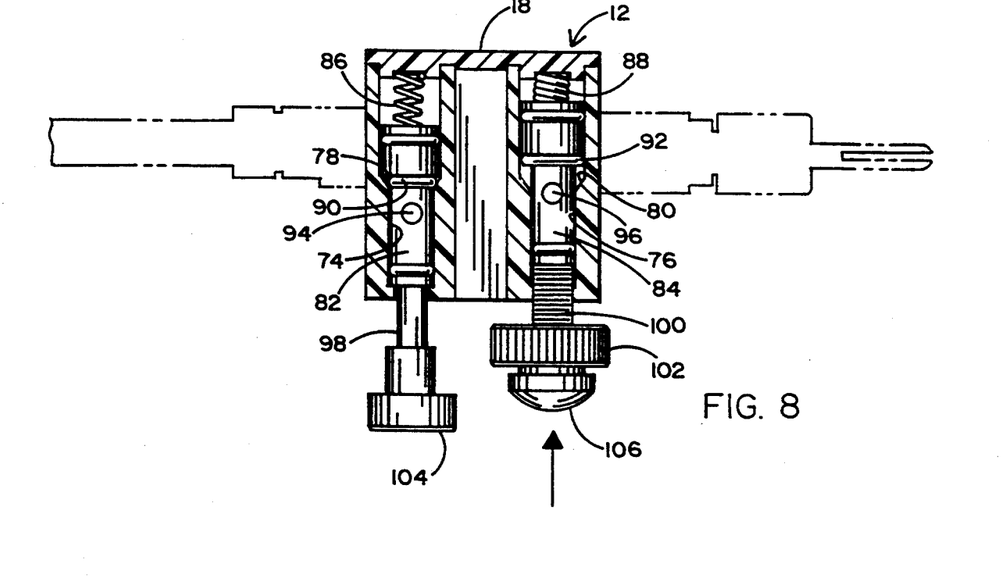
FIG. 8 is a section taken generally along line 8—8 of FIG. 4.

Valves are provided to control fluid flow. Valve bores 74 and 76 respectively intersect irrigation passage 70 and vacuum passage 72, see FIGS. 6, 7, 8 and 9. The valve bores also intersect main passage 30, as best seen in FIGS. 7 and 9. The valve bores each have a smaller and a larger diameter with these two diameters joining at an angular shoulder. Shoulder 78 is shown in FIG. 7, and shoulder 80 is shown in FIG. 9. As is best seen in FIGS. 7, 8 and 9, slide valves are positioned in these valve bores. Valve plungers 82 and 84 are respectively slidably mounted in bores 74 and 76. Compression springs 86 and 88 are positioned at the bottom of the plungers and engage against the bottom of the valve bores to urge the valve plungers to the off position, which is shown for valve plunger 78 in FIGS. 7 and 9. The valve plungers carry O-rings thereon which engage against the shoulders 78 and 80 when the plungers are in the valve-closed position.

The main passage 30 intersects the larger bore of the valve bore and, thus, is below the shoulder against which the O-ring seals. In FIG. 7, the valve 84 is in the closed position with the O-ring 90 sealed against the shoulder 80. Main passage 30 intersects the bores 74 and 76 at their larger diameter below their shoulders. When the valve plunger O-ring is against the shoulder, the valve passages are closed without the chance of leaking through a loose bore. When the valve plungers are depressed to open the valves, the valve O-ring moves off of the shoulder and the diagonal passage through the valve stem opens the connection. The diagonal passages 94 and 96 are shown in full lines in FIG. 8. The diagonal passage 96 is shown in dashed lines in FIGS. 7 and 9. In FIG. 7, the vacuum valve is closed; and in FIG. 9, it is open. In the open position, the diagonal passage 96 interconnects the vacuum passage 72 with the main passage 30.

The valve plungers have shanks 98 and 100, which are of smaller diameter than the valve plunger and extend out of the top of the valve body 100. The shank 100 is threaded and carries adjustable stop nut 102 thereon. Actuator buttons 104 and 106 are respectively mounted on the shanks 98 and 100 so that they are each individually rigidly engaged for digital actuation. Each of the shanks 98 and 100 has a slot therein on the lower side, and these slots are respectively engaged by pins. These pins prevent the valve plungers from rotating, and this is necessary because the diagonal passages 94 and 96 need to stay in alignment with the passages 70 and 72. The pins are also helpful in preventing the rotation of the valves because they are easier to manipulate when they do not rotate. In a surgical application, the ease and accuracy of manipulation are critically important.

In use, the endoscopic suction, irrigation and cautery instrument 20 is used in endoscopic surgery. Two sizes of cannula 38 are available. A cannula lumen with a 5 millimeter opening is satisfactory for normal suction and irrigation functions during endoscopic surgery. The fact that the cannula and body of the instrument are transparent now provides to the surgeon a completely see-through device. This enables the surgeon if there is something caught in one of the trumpet valve passages. The transparency is very helpful to permit the surgeon to see if a specimen of tissue has been caught in the valve body and elsewhere between the tip of the cannula and the suction valve. The cannula and valve body are now a window the surgeon can employ to see what is being withdrawn. This is helpful because, if the suction passage is not clear, at the end of suction, material may drip back into the operating field. On the other hand, if irrigation follows, the material left in the valve body and cannula would be sprayed back into the field. The clear cannula and clear instrument body eliminate this difficulty. When the smaller lumen is used, a suitable plug is provided in the threaded socket in the valve body which is not holding the cannula. Since both of the female threaded sockets 32 and 34 are the same, the cannula can be inserted into either end of the valve body, and the plug into the opposite end so that the instrument can be assembled for either a right- or a left-handed surgeon.

The instrument is also provided with an interchangeable cannula 38 which has a 10 millimeter inside diameter. This cannula is also clear so that, together with the clear valve body, the passage of suction material can be observed. The larger diameter cannula lumen permits the removal of larger material, such as clots and gallstones. In addition, the larger lumen permits the employment of a cautery electrode which extends through the larger suction and irrigation cannula 38. The installation of the cautery electrode 16 has been described previously. It can be advanced to the left or withdrawn to the right. It can be rotated by its adjusting wheel 58 so that the tip is oriented in the correct position. The cautery electrode 16 is preferably insulated over its length, except for its ends. When cautery is used, an electric current is applied by the tip of the electrode to the issue which is to be sealed. The electric charge causes capacitive coupling with any nearby conductive material. In the present instance, the cannula 38 is non-conductive so that it receives no charge. Use of the 10 millimeter cannula separates the surrounding tissue from the sides of the electrode so that there is little coupling. Thus, there is no capacitive coupling problem during the use of cautery through the sides of the cannula because it is non-conductive.

During laparoscopic surgery, there is a need to distend the patient's abdomen. Carbon dioxide is usually used. This is done to open space between the organs to permit passage of the laparoscope and endoscopic instruments and is called "insufflation" or "pneumoperitoneum." When a cautery electrode is used, it creates a considerable amount of smoke in this enclosed environment. The surgeon uses the suction function of the instrument to withdraw the smoke. However, if too much suction volume is employed, the entire pneumoperitoneum is withdrawn. The insufflation machine has a limited insufflation rate. Thus, it is desirable to control the suction rate. The adjustable stop 102 limits the downstroke of the valve 84 to limit the suction volume. Adjustment of the nut 102 adjusts this rate. The surgeon simply thumbs the adjustable stop nut 102 to the correct value to control the suction rate. The adjustable stop nut 102 is configured so that, when it is in its position of minimum suction flow, the suction rate is about 1½ liters per minute. In this way, the surgeon can maintain the suction and not be concerned about losing the space created by the pneumoperitoneum.

As described above, the removal of cap 48 permits complete withdrawal of the cautery electrode 16. It also permits the replacement with other cautery electrodes. The electrode 16 is standard for connection to a monopolar cable hookup. The wheel 58 provides for rotation and advancement of retraction of the cautery electrode. The cautery electrode can be withdrawn into the tip opening of the cannula and can be advanced and positioned by wheel 58 to stop the bleeding quickly and effectively without over-cauterizing surrounding tissues. After cauterization, the cautery electrode can be retracted. At the same time, when the cautery electrode is positioned, the irrigation and suction can then clear the field for accurate placement. The instrument can remove the excess blood, irrigate to find the source of bleeding, and film advance the cautery electrode to cauterize just what is bleeding. The withdrawal of the cautery electrode is important because, if the electrode remains extended, a cannula with an extended cautery electrode cannot be passed blindly around an organ to suction fluid behind or underneath the organ. An exposed cautery tip on such a cannula would injure the organ or cause unreachable bleeding. Thus, with this combination of benefits, an advanced endoscopic suction, irrigation and cautery instrument is achieved.

In addition to the convenience of individual finger operation of the valves, suction valve adjustable stop and cautery electrode, each of these functions can be accomplished by the fingers of the surgeon as he holds the valve body in his hands. Two-handed operation is not necessary, and each of the functions can be individually and jointly accomplished while the surgeon holds the endoscopic suction, irrigation and cautery instrument in his hand.

This invention has been described in its presently contemplated best embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An endoscopic suction, irrigation and cautery instrument comprising:
   a transparent valve body having ends, a main passage in said valve body extending through said body from end to end, attachment means at each end of said main passage for the attachment of a cannula thereto, said main passage defining an axis through said main body, an irrigation fluid connection and a vacuum connection on said body, an irrigation fluid channel and a suction channel respectively extending from each said connection into said main body, said channels being non-intersecting with said main passage;
   an irrigation bore in said body intersecting both said main passage and said irrigation channel, a vacuum bore in said body intersecting both said main passage and said vacuum channel, said irrigation bore having a shoulder therein between said irrigation channel and said main passage, said vacuum bore having a shoulder therein between said vacuum channel and said main passage, said shoulders acting as valve seats;

an irrigation valve plunger in said irrigation valve bore, said irrigation valve plunger having a shoulder thereon acting as a valve disc and cooperating with said irrigation bore shoulder to close when said irrigation valve plunger is in a first position;

a vacuum valve plunger in said vacuum valve bore, said vacuum valve plunger having a shoulder thereon in cooperation with said shoulder in said vacuum valve bore to close said vacuum channel from said main passage to said vacuum channel when said vacuum valve plunger is in a first position; and a tubular cannula detachably attached to said valve body at said attachment means on said valve body, said valve body being sized and said valve plungers being positioned so that said valve body can be grasped in the hand and fingers on the hand can actuate said valve plungers from said first position toward a second position wherein said shoulders are unseated to selectively open said valves for selective irrigation and suction so that a surgeon can maneuver said cannula and control flow therethrough with a single hand.

2. The instrument of claim 1 wherein said suction valve plunger has an adjustable stop thereon to selectively limit opening of said suction valve.

3. The instrument of claim 2 wherein said adjustable stop is a nut threaded onto said suction valve plunger so that said nut engages said body when said suction valve plunger is in its open position.

4. An endoscopic suction, irrigation and cautery instrument comprising:

a transparent valve body having ends, a main passage in said valve body extending through said body from end to end, attachment means at each end of said main passage for the attachment of a cannula thereto, said main passage defining an axis through said main body, an irrigation fluid connection and a vacuum connection on said body, an irrigation fluid channel and a suction channel respectively extending from each said connection into said main body, said channels being non-intersecting with said main passage;

an irrigation bore in said body intersecting both said main passage and said irrigation channel, a vacuum bore in said body intersecting both said main passage and said vacuum channel, said irrigation bore having a shoulder therein between said irrigation channel and said main passage, said vacuum bore having a shoulder therein between said vacuum channel and said main passage, said shoulders acting as valve seats;

an irrigation valve plunger in said irrigation valve bore, said irrigation valve plunger having a shoulder thereon acting as a valve disc and cooperating with said irrigation bore shoulder, an O-ring between said shoulders to resiliently seal said valve when said irrigation valve plunger is in a first position;

a vacuum valve plunger in said vacuum valve bore, said vacuum valve plunger having a shoulder thereon in cooperation with said shoulder in said vacuum valve bore, an O-ring between said shoulders to resiliently seal said vacuum channel from said main passage to said vacuum channel when said vacuum valve plunger is in a first position; and a tubular cannula detachably attached to said valve body at said attachment means on said valve body, said valve body being sized and said valve plungers being positioned so that said valve body can be grasped in the hand and fingers on the hand can actuate said valve plungers from said first position toward a second position wherein said shoulders are unseated to selectively open said valves for selective irrigation and suction so that a surgeon can maneuver said cannula and control flow therethrough with a single hand.

5. The instrument of claim 4 wherein there is a spring in said body engaging said vacuum valve plunger to urge said plunger toward its first position so that fingerforce is necessary to move said valve plunger away from its first position to open said valve.

6. The instrument of claim 4 wherein there is a spring in said body urging said vacuum irrigation plunger toward its first position so that finger-force is necessary to move said valve plunger away from its first position to open said valve.

7. The instrument of claim 6 wherein there is a diagonal opening through said irrigation valve plunger, said diagonal opening being in line with both said irrigation channel and said main passage when said irrigation valve plunger is in its second, full open position.

8. An endoscopic suction, irrigation and cautery instrument comprising:

a transparent valve body having ends, a main passage in said valve body extending through said body from end to end, attachment means at each end of said main passage for the attachment of a cannula thereto, said main passage defining an axis through said main body, an irrigation fluid connection and a vacuum connection on said body, an irrigation fluid channel and a suction channel respectively extending from each said connection into said main body, said channels being non-intersecting with said main passage;

an irrigation bore in said body intersecting both said main passage and said irrigation channel, a vacuum bore in said body intersecting both said main passage and said vacuum channel, said irrigation bore having a shoulder therein between said irrigation channel and said main passage, said vacuum bore having a shoulder therein between said vacuum channel and said main passage, said shoulders acting as valve seats;

an irrigation valve plunger in said irrigation valve bore, said irrigation valve plunger having a shoulder thereon acting as a valve disc and cooperating with said irrigation bore shoulder when said irrigation valve plunger is in a first position, a diagonal opening through said irrigation valve plunger, said diagonal opening being in line with both said irrigation channel and said main passage when said irrigation valve plunger is in its second, full open position;

a vacuum valve plunger in said vacuum valve bore, said vacuum valve plunger having a shoulder thereon in cooperation with said shoulder in said vacuum valve bore to close said vacuum channel when said vacuum valve plunger is in a first position; and a tubular cannula detachably attached to said valve body at said attachment means on said valve body, said valve body being sized and said valve plungers being positioned so that said valve body can be grasped in the hand and fingers on the hand can actuate said valve plungers from said first position toward a second position wherein said shoulders are unseated to selectively open said valves for selective irrigation and suction so that a surgeon can maneuver said cannula and control flow therethrough with a single hand.

9. An endoscopic suction, irrigation and cautery instrument comprising:

a transparent valve body having ends, a main passage in said valve body extending through said body from end to end, attachment means at each end of said main passage for the attachment of a cannula thereto, said main passage defining an axis through said main body, an irrigation fluid connection and a vacuum connection on said body, an irrigation fluid channel and a suction channel respectively extending from each said connection into said main body, said channels being non-intersecting with said main passage;

an irrigation bore in said body intersecting both said main passage and said irrigation channel, a vacuum bore in said body intersecting both said main passage and said vacuum channel, said irrigation bore having a shoulder therein between said irrigation channel and said main passage, said vacuum bore having a shoulder therein between said vacuum channel and said main passage, said shoulders acting as valve seats;

an irrigation valve plunger in said irrigation valve bore, said irrigation valve plunger having a shoulder thereon acting as a valve disc and cooperating with said irrigation bore shoulder to close said irrigation channel when said irrigation valve plunger is in a first position;

a vacuum valve plunger in said vacuum valve bore, said vacuum valve plunger having a shoulder thereon in cooperation with said shoulder in said vacuum valve bore to close said vacuum channel from said main passage to close said vacuum channel when said vacuum valve plunger is in a first position, said vacuum valve plunger having a second position wherein it is fully deflected away from said first position, said vacuum valve plunger having a diagonal opening therethrough, said diagonal opening being in line with both said main passage and with said vacuum channel when said vacuum valve plunger is in its second position; and a tubular cannula detachably attached to said valve body at said attachment means on said valve body, said valve body being sized and said valve plungers being positioned so that said valve body can be grasped in the hand and fingers on the hand can actuate said valve plungers from said first position toward a second position wherein said shoulders are unseated to selectively open said valves for selective irrigation and suction so that a surgeon can maneuver said cannula and control flow therethrough with a single hand.

10. An endoscopic suction, irrigation and cautery instrument comprising:

a valve body having a first end and a second end, a main passage through said valve body, said main passage having a first end and a second end respectively at the ends of said main body, first and second fastening means respectively at said first and second ends of said main passage;

said body having an irrigation connection thereon and a suction connection thereon, an irrigation channel in said body connected to said irrigation connection and a suction channel in said body connected to said suction connection, said irrigation channel and said suction channel being away from said main passage;

an irrigation valve bore in said body connecting said irrigation channel and said main passage, said irrigation valve bore having a shoulder therein, a suction valve bore in said body connecting said suction channel and said main passage, said suction valve bore having a shoulder therein;

an irrigation valve plunger in said irrigation valve bore, said irrigation valve plunger having a shoulder thereon to cooperate with said shoulder in said bore to cause closure between said irrigation channel and said main passage when said valve plunger is in a first position, said suction valve bore having a suction valve plunger therein, said suction valve plunger having a shoulder thereon cooperating with said shoulder in said suction valve bore to cause closure between said suction channel and said main passage when said suction valve plunger is in a first position, said plungers being sized and positioned so that they can be finger-actuated by a person holding said valve body in his hand.

11. An endoscopic suction, irrigation and cautery instrument comprising:

a valve body having a first end and a second end, a main passage through said valve body, said main passage having a first end and a second end respectively at the ends of said main body, first and second fastening means respectively at said first and second ends of said main passage;

said body having an irrigation connection thereon and a suction connection thereon, an irrigation channel in said body connected to said irrigation connection and a suction channel in said body connected to said suction connection, said irrigation channel and said suction channel being away from said main passage;

an irrigation valve bore in said body connecting said irrigation channel and said main passage, said irrigation valve bore having a shoulder therein, a suction valve bore in said body connecting said suction channel and said main passage, said suction valve bore having a shoulder therein;

an irrigation valve plunger in said irrigation valve bore, said irrigation valve plunger having a shoulder thereon to cooperate with said shoulder in said bore, an O-ring on said valve plunger between said shoulders to cause closure between said irrigation channel and said main passage when said valve plunger is in a first position, said suction valve bore having a suction valve plunger therein, said suction valve plunger having a shoulder thereon cooperating with said shoulder in said suction valve bore, an 0-ring on said valve plunger between said shoulders to cause closure between said suction channel and said main passage when said suction valve plunger is in a first position, said plungers being sized and positioned so that they can be finger-actuated by a person holding said valve body in his hand.

12. The instrument of claim 11 wherein there is a spring in said body acting against each of said plungers to urge said plungers toward said first positions.

13. The instrument of claim 11 wherein said valve plungers have a second position when deflected by the user's fingers away from the first position, said shoulders being away from each other in said second position, a diagonal opening through said suction valve plunger, said diagonal hole intersecting with said irrigation channel and with said main passage when said irrigation valve plunger is in its second position.

14. The instrument of claim 13 wherein said vacuum valve has a diagonal bore therein, said vacuum valve being in line with said vacuum channel and said main passage when said vacuum plunger is in its second position.

15. The instrument of claim 14 wherein there is a threaded nut on said vacuum valve plunger, said threaded nut being adjustable to limit motion of said vacuum valve plunger from said first position toward said second position to control vacuum.

* * * * *